United States Patent
Egusa et al.

(10) Patent No.: US 10,899,153 B2
(45) Date of Patent: Jan. 26, 2021

(54) HEAT-SENSITIVE RECORDING MATERIAL AND DIPHENYLSULFONE

(71) Applicant: Nippon Kayaku Kabushiki Kaisha, Tokyo (JP)

(72) Inventors: Tsunetoshi Egusa, Fukuyama (JP); Takashi Fujii, Fukuyama (JP); Hiroyuki Tsukui, Fukuyama (JP); Takaaki Kurata, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 251 days.

(21) Appl. No.: 15/772,852

(22) PCT Filed: Nov. 15, 2016

(86) PCT No.: PCT/JP2016/083791
§ 371 (c)(1),
(2) Date: May 2, 2018

(87) PCT Pub. No.: WO2017/086302
PCT Pub. Date: May 26, 2017

(65) Prior Publication Data
US 2018/0312465 A1    Nov. 1, 2018

(30) Foreign Application Priority Data
Nov. 20, 2015   (JP) ................................ 2015-227300

(51) Int. Cl.
*B41M 5/333*   (2006.01)
*B41M 5/42*   (2006.01)

(52) U.S. Cl.
CPC ............ *B41M 5/3336* (2013.01); *B41M 5/42* (2013.01); *B41M 2205/04* (2013.01)

(58) Field of Classification Search
CPC .. B41M 5/333; B41M 5/3333; B41M 5/3335; B41M 5/3336
See application file for complete search history.

(56) References Cited

U.S. PATENT DOCUMENTS

| | | |
|---|---|---|
| 4,608,580 A | 8/1986 | Ikeda et al. |
| 6,114,282 A | 9/2000 | Onishi et al. |
| 2006/0217574 A1 | 9/2006 | Enokida et al. |

FOREIGN PATENT DOCUMENTS

| | | |
|---|---|---|
| CN | 1226857 A | 8/1999 |
| CN | 1351544 A | 5/2002 |
| JP | 61-89090 A | 5/1986 |
| JP | 62-53957 A | 3/1987 |
| JP | 1-150576 A | 6/1989 |
| JP | 1-178491 A | 7/1989 |
| JP | 11-208121 A | 8/1998 |
| JP | 11-29549 A | 2/1999 |
| JP | 2002-30064 A | 1/2002 |
| JP | 2015-124208 A | 7/2015 |
| WO | 2004/089883 A1 | 10/2004 |

OTHER PUBLICATIONS

Machine translation of detailed description of JP61-089090 created on Mar. 5, 2020.*
Chinese communication, with partial English translation, dated Jul. 1, 2019 in corresponding Chinese patent application No. 201680067743.8.
European communication dated Jul. 1, 2019 in corresponding European patent application No. 16866303.7.
International Search Report and Written Opinion dated Dec. 27, 2016 in corresponding PCT application No. PCT/US2014/061296.
Chinese communication, with English translation, dated Aug. 3, 2020 in corresponding Chinese patent application No. 201680067743.8.

* cited by examiner

*Primary Examiner* — Gerard Higgins
(74) *Attorney, Agent, or Firm* — Nields, Lemack & Frame, LLC

(57) ABSTRACT

The content of compound(s) having a molecular weight of 650-670, typically a molecular weight of 660, as measured by mass spectrometry, is reduced to 0.5 mass % or less in a heat-sensitive recording material comprising 3,3'-diallyl-4,4'-dihydroxy diphenylsulfone, or in a diphenylsulfone or a color-developing agent. Provided is, thereby, a heat-sensitive recording material, a color-developing agent, or a diphenylsulfone which cause less background fogging under moisture and heat conditions and which has excellent preservation stability of a colored image.

12 Claims, No Drawings

HEAT-SENSITIVE RECORDING MATERIAL AND DIPHENYLSULFONE

TECHNICAL FIELD

The present invention relates to a heat-sensitive recording material comprising 3,3'-diallyl-4,4'-dihydroxydiphenylsulfone as a color-developing agent, more specifically to a heat-sensitive recording material comprising 3,3'-diallyl-4,4'-dihydroxydiphenylsulfone as a color-developing agent wherein background fogging (darkening of a portion which has not developed color) and image preservation stability are improved by reducing the content of a specific impurity.

BACKGROUND ART

A heat-sensitive recording material is generally obtained by making dispersed fine particles of a colorless or light-colored leuco dye and fine particles a color-developing agent such as a phenolic substance respectively, then mixing these fine particles, and adding thereto additives such as a binder, a sensitizer, a filler and a lubricant; and is used to be applied to paper, a film, synthetic paper, or the like. The heat-sensitive recording material produces a color development through chemical reactions that occur by melting one or both of the leuco dye and the color-developing agent by heating to bring into contact with each other. To induce the color developments, a thermal printer or the like equipped with a thermal head is used. As compared to other recording methods, this heat-sensitive recording method has such advantages that (1) no noise in recording, (2) no requirement to develop or fix an image, (3) maintenance-free, and (4) a machine being relatively inexpensive, and has been widely used in the field of facsimile, the field of printers for computer output, a calculator and the like, the field of recorders for medical measurements, the field of automatic ticket vending machines, the field of heat-sensitive recording labels, and the like.

In recent years, along with introduction of POS systems into retail stores, supermarkets and the like, automation systems of transportation and automation of logistics systems, a heat-sensitive recording material has been used for various applications such as labels used for food or the like, tickets, coupon tickets, and logistics labels. In tune with the expanded applications, it has been desired to exhibit preservation stability under severer conditions than before: Examples of the preservation stability includes preservation stability of a printed portion to plasticizers contained in vinyl chloride films used for food packaging and preservation stability of a printed portion to hand creams, which could be a problem when a consumer directly touches the printed portion. In addition, there have been increasing needs for high-speed recording, and it has been strongly desired to develop a heat-sensitive recording material capable of sufficiently satisfying the needs for high-speed recording. However, in general, when sensitivity of a heat-sensitive recording material is increased to improve thermal responsiveness, disadvantage of background fogging tends to be caused.

Widely used ordinary color developing agents include a bisphenol S derivative. For example, a heat-sensitive recording material containing 3,3'-diallyl-4,4'-dihydroxydiphenylsulfone as a color-developing agent has been proposed (Patent Literatures 1 to 5).

The inventors have also disclosed that background fogging can be reduced by inclusion of, as a color developing agent, a specific crystal of 3,3'-diallyl-4,4'-dihydroxydiphenylsulfone characterized by specific peaks in an X-ray diffraction pattern (Patent Literature 5).

CITATION LIST

Patent Literature

PATENT LITERATURE 1: JP-A-61-89090
PATENT LITERATURE 2: JP-A-62-53957
PATENT LITERATURE 3: JP-A-01-150576
PATENT LITERATURE 4: JP-A-01-178491
PATENT LITERATURE 5: JP-B-3992252

SUMMARY OF INVENTION

Technical Problem

In the above-described state of the art, an object of the present invention is to provide a heat-sensitive recording material having high sensitivity, less background fogging, and improved image preservation stability.

Solution to Problem

In order to satisfy high needs for sensitivity and preservation stability in recent years, the present inventors have conducted various studies and have newly found a specific compound to be a by-product in known heat-sensitive recording materials containing 3,3'-diallyl-4,4'-dihydroxydiphenylsulfone as a color-developing agent. Therefore, the present inventors manufactured a heat-sensitive recording material with a reduced content of this compound. Surprisingly a heat-sensitive recording material having high sensitivity, less background fogging, and largely improved preservation stability of a printed portion has been obtained, and the present invention has been reached.

That is, the present invention relates to:

(1) a heat-sensitive recording material comprising 3,3'-diallyl-4,4'-dihydroxydiphenylsulfone, wherein the content of a compound generated as a by-product during synthesis of the 3,3'-diallyl-4,4'-dihydroxydiphenylsulfone and having a molecular weight of 650 to 670, typically having a molecular weight of 660, is less than 0.8% by mass in mass spectrometry;

(2) the heat-sensitive recording material according to (1), wherein the content of the compound having a molecular weight of 650 to 670, typically having a molecular weight of 660, is 0.5% by mass or less;

(3) the heat-sensitive recording material according to (1) or (2), wherein the 3,3'-diallyl-4,4'-dihydroxydiphenylsulfone has a crystal form characterized by an X-ray diffraction diagram having peaks at least at diffraction angles (2θ) [°] of 7.2 and 22.0 in a powder X-ray diffraction method with a Cu-Kα ray;

(4) the heat-sensitive recording material according to (3), wherein the 3,3'-diallyl-4,4'-dihydroxydiphenylsulfone has a crystal form characterized by an X-ray diffraction diagram having peaks at least at diffraction angles (2θ) [°] of 7.2, 16.3, 20.0, 22.0, 24.7, and 29.0 in a powder X-ray diffraction method with a Cu-Kα ray;

(5) the heat-sensitive recording material according to (3), wherein the 3,3'-diallyl-4,4'-dihydroxydiphenylsulfone has a crystal form characterized by an X-ray diffraction diagram having peaks at least at diffraction angles (2θ) [°] of 7.2, 14.5, 16.3, 18.0, 20.0, 21.0, 22.0, 24.7, and 29.0 in a powder X-ray diffraction method with a Cu-Kα ray;

(6) a heat-sensitive recording layer comprising the heat-sensitive recording material according to any one of (1) to (5);

(7) a heat-sensitive recording paper comprising the heat-sensitive recording layer according to (6);

(8) a heat-sensitive recording film comprising the heat-sensitive recording layer according to (6);

(9) 3,3'-diallyl-4,4'-dihydroxydiphenylsulfone wherein the content of a compound having a molecular weight of 650 to 670, typically having a molecular weight of 660, generated as a by-product during synthesis is less than 0.8% by mass in mass spectrometry;

(10) the 3,3'-diallyl-4,4'-dihydroxydiphenylsulfone according to (9), in which the content of the compound having a molecular weight of 650 to 670, typically having a molecular weight of 660, is 0.5% by mass or less;

(11) the 3,3'-diallyl-4,4'-dihydroxydiphenylsulfone according to (9) or (10), having a crystal form characterized by an X-ray diffraction diagram having peaks at least at diffraction angles (2θ) [°] of 7.2 and 22.0 in a powder X-ray diffraction method with a Cu-Kα ray;

(12) the 3,3'-diallyl-4,4'-dihydroxydiphenylsulfone according to (11), having a crystal form characterized by an X-ray diffraction diagram having peaks at least at diffraction angles (2θ) [°] of 7.2, 16.3, 20.0, 22.0, 24.7, and 29.0 in a powder X-ray diffraction method with a Cu-Kα ray;

(13) the 3,3'-diallyl-4,4'-dihydroxydiphenylsulfone according to (11), characterized by an X-ray diffraction diagram having peaks at least at diffraction angles (2θ) [°] of 7.2, 14.5, 16.3, 18.0, 20.0, 21.0, 22.0, 24.7, and 29.0 in a powder X-ray diffraction method with a Cu-Kα ray;

(14) a color-developing agent comprising 3,3'-diallyl-4,4'-dihydroxydiphenylsulfone, in which the content of a compound having a molecular weight of 650 to 670, typically having a molecular weight of 660, generated as a by-product during synthesis of the 3,3'-diallyl-4,4'-dihydroxydiphenylsulfone is less than 0.8% by mass in mass spectrometry;

(15) the color-developing agent according to (14), in which the content of the compound having a molecular weight of 650 to 670, typically having a molecular weight of 660 is 0.5% by mass or less; and (16) the color-developing agent according to (14) or (15), in which the 3,3'-diallyl-4,4'-dihydroxydiphenylsulfone has a crystal form characterized by an X-ray diffraction diagram having peaks at least at diffraction angles (2θ) [°] of 7.2 and 22.0 in a powder X-ray diffraction method with a Cu-Kα ray.

Advantageous Effects of Invention

According to the present invention, 3,3'-diallyl-4,4'-dihydroxydiphenylsulfone containing less than 0.8% by mass of, preferably 0.5% by mass or less of, a compound generated as a by-product during synthesis and having a molecular weight of 650 to 670, typically having a molecular weight of 660, as measured by mass spectrometry, is used as a color-developing agent, whereby a heat-sensitive recording material excellent in moist heat resistance of a background, and plasticizer resistance and hand cream resistance of a printed portion can be provided.

DESCRIPTION OF EMBODIMENTS

An embodiment of the present invention will be described in detail. However, the present invention should not be understood as being limited to the following embodiments.

According to one embodiment of the present invention, 3,3'-diallyl-4,4'-dihydroxydiphenylsulfone has a crystal form characterized by an X-ray diffraction diagram preferably having (relatively strong) peaks at least at diffraction angles (2θ)[°] of 7.2 and 22.0, more preferably having (relatively strong) peaks at least at diffraction angles (2θ)[°] of 7.2, 16.3, 20.0, 22.0, 24.7 and 29.0, still more preferably having (relatively strong) peaks at least at diffraction angles (2θ)[°] of 7.2, 14.5, 16.3, 20.0, 22.0, 24.7 and 29.0, particularly preferably having (relatively strong) peaks at least at diffraction angles (2θ)[°] of 7.2, 14.5, 16.3, 18.0, 20.0, 21.0, 22.0, 24.7 and 29.0 in a powder X-ray diffraction method with a Cu-Kα ray. It is to be noted that an error of about plus or minus 0.1 is permitted in a diffraction angle (2θ) [°].

Conditions for measurement of diffraction angles (2θ) [°] for a crystal form obtained by the present invention by a powder X-ray diffraction method are as follows.

Device name: RAD-2C manufactured by Rigaku Denki Co., Ltd.
Target: Cu
Scanning angle: 2° to 40.0°
Scanning speed: 2°/min
Tube voltage: 40 KV
Tube current: 30 mA
Slits: DS 1, RS 0.15, and SS 1

In one embodiment of the present invention, 3,3'-diallyl-4,4'-dihydroxydiphenylsulfone (di-rearrangement product: primary product) has purity of preferably 96.0% by mass or more, and more preferably 96.5% by mass or more. The 3,3'-diallyl-4,4'-dihydroxydiphenylsulfone could contain, as impurities (by-products), a mono product (3-allyl-4,4'-dihydroxydiphenylsulfone), an indane product (5-(3-allyl-4-hydroxy) phenylsulfone-1-oxa-2-methylindane), a unilateral rearrangement product (3-allyl-4'-allyloxy-4-hydroxydiphenylsulfone), a compound having a molecular weight of 650 to 670, typically having a molecular weight of 660, and the like. The total content of the mono product (3-allyl-4,4'-dihydroxydiphenylsulfone), the indane product (5-(3-allyl-4-hydroxy) phenylsulfone-1-oxa-2-methylindane), and the unilateral rearrangement product (3-allyl-4'-allyloxy-4-hydroxydiphenylsulfone) is 2% by mass or less, in which the content of the mono product is 2% by mass or less, the content of the indane product is 1% by mass or less, and the content of the unilateral rearrangement product is 1% by mass or less.

In one embodiment of the present invention, 3,3'-diallyl-4,4'-dihydroxydiphenylsulfone can contain a compound generated during synthesis of the primary product (for example, Claisen rearrangement reaction of 4,4'-diallyloxydiphenylsulfone) and having a molecular weight of 650 to 670, typically having a molecular weight of 660, in a content of less than 0.8% by mass, preferably 0.5% by mass or less, and more preferably 0.4% by mass or less, as measured by mass spectrometry. This compound having a molecular weight of 650 to 670 can be a compound obtained by dimerization of 4,4'-diallyloxydiphenylsulfone having a molecular weight of 330, i.e. a raw material for synthesis of 3,3'-diallyl-4,4'-dihydroxydiphenylsulfone, and typically has a molecular weight of 660. However, the compound(s) having a molecular weight of 650 to 670 includes compounds obtained by subjecting the compound having a molecular weight of 660 to some modifications and thereby having different molecular weights around 660.

It is to be noted that it has been found for the first time that the compound(s) having a molecular weight of 650 to 670, typically having a molecular weight of 660, have an influence on background fogging and image preservation stability.

Presence of the compound(s) having a molecular weight of 650 to 670, typically having a molecular weight of 660, can be detected by mass spectrometry using, for example, an LC/MS analyzer Quadrupole 6120 manufactured by Agilent Technologies Japan, Ltd.

The purity of 3,3'-diallyl-4,4'-dihydroxydiphenylsulfone and the presence and the content of impurities (by-products) such as a mono product, an indane product, and a unilateral rearrangement product can be determined, for example, from measurement chart obtained by HPLC analysis and an area ratio calculated therefrom (purity and content are determined by area %). Measurement conditions of HPLC analysis for analyzing these can be set, for example, as follows.

Device name: HPLC analyzer manufactured by Shimadzu Corporation
    Analytical column: Nucleosil 5C18 4.0 mm×250 mm
    Mobile phase: 70% methanol/water
    Flow rate: 0.6 ml/min
    Column temperature: 40° C.
    Detector: UV 254 nm In this HPLC analysis, each product can be detected at the following measurement times: a peak of a di-rearrangement product (main body) at about 7.7 minutes, a peak of a mono product at about 5.5 minutes, a peak of an indane product at about 9.2 minutes, a peak of a unilateral rearrangement product at about 10.4 minutes, a peak of a compound having a molecular weight of 650 to 670, typically having a molecular weight of 660 at about 15.7 minutes.

In one embodiment of the present invention, 3,3'-diallyl-4,4'-dihydroxydiphenylsulfone is synthesized, for example, by performing a Claisen rearrangement reaction of 4,4'-diallyloxydiphenylsulfone. Specifically, for example, this rearrangement reaction is performed in an inert water-insoluble organic solvent having a high boiling point usually at 160 to 280° C., preferably at 190 to 230° C., more preferably at 200 to 220° C.; and the reaction is terminated when the generation amount of 3,3'-diallyl-4,4'-dihydroxydiphenylsulfone, which is a di-rearrangement product, reaches about 90% by mass (for example, 89 to 93% by mass). A reaction product is extracted with an alkali aqueous solution and then purified with an activated carbon. Subsequently, this extraction liquid is introduced into a high-temperature acidic aqueous solution (for example, a diluted hydrochloric acid aqueous solution) to precipitate a crystal. Alternatively, a Claisen rearrangement reaction is performed in the same manner, and then a reaction product is extracted with an alkali aqueous solution. Water and a water-insoluble organic solvent (for example, an aromatic organic solvent such as dichloro benzene) are added thereto, and an acidic aqueous solution (for example, a hydrochloric acid aqueous solution) is added thereto until a neutralization equivalent reaches 40 to 60%. Thereafter, a water layer and an oil layer are separated from each other. To the water layer, an acidic aqueous solution (for example, a hydrochloric acid aqueous solution) is further added to precipitate a crystal. A water-insoluble organic solvent used in the above reaction is not particularly limited as long as having a boiling point of 160° C. or higher, preferably 190° C. or higher, more preferably 200° C. or higher, still more preferably 200 to 220° C. and being inert to raw materials and the primary product. Examples of the water-insoluble organic solvent include a mixed solvent of an aliphatic hydrocarbon-based organic solvent (for example, MC oil W-8 (manufactured by Idemitsu Kosan Co., Ltd.)) and kerosene (white kerosene).

In the present invention, a precipitated crystalline compound is further purified to remove compound(s) having a molecular weight of 650 to 670, typically having a molecular weight of 660. A purification method may be ones generally used for an organic compound, such as activated carbon purification, column chromatography purification and sublimation purification. However, it is necessary to set conditions suitable for removing compound(s) having a molecular weight of 650 to 670, typically having a molecular weight of 660. Conditions under which purification is performed will be apparent from the molecular weights of and other physicochemical properties compound(s) to be removed and 3,3'-diallyl-4,4'-dihydroxydiphenylsulfone.

In one embodiment of the present invention, a heat-sensitive recording material is prepared using, as main components, a color-forming compound, which would be generally colorless or light-colored, and a color-developing agent of 3,3'-diallyl-4,4'-dihydroxydiphenylsulfone, as described above, containing a reduced content of a compound generated during the synthesis and having a molecular weight of 650 to 670, typically having a molecular weight of 660, and a sensitizer, a binder, a filler, an additive, and the like described below, if necessary. In one embodiment of the present invention, the content of 3,3'-diallyl-4,4'-dihydroxydiphenylsulfone is 0.5 to 20 parts by mass, and preferably 1 to 5 parts by mass with respect to 1 part by mass of the color-forming compound.

In one embodiment of the present invention, in preparing a heat-sensitive recording material, a color-forming compound can be used in an amount of 1 to 50% by mass, preferably 5 to 30% by mass; 3,3'-diallyl-4,4'-dihydroxydiphenylsulfone as a color-developing agent can be used in an amount of 1 to 80% by mass, preferably 5 to 40% by mass; a sensitizer can be used in an amount of 0.5 to 80% by mass, preferably 5 to 40% by mass; a binder can be used in an amount of 1 to 90% by mass; other color-developing agents and a sensitizer which can be used in combination are each used in an amount of 0 to 40% by mass; a filler can be used in an amount of 0 to 80% by mass; a lubricant, a surfactant, an antifoaming agent, an ultraviolet absorber, and the like can be each used at any ratio, for example, in an amount of 0 to 30% by mass (% by mass is a mass ratio of each component in a heat-sensitive recording layer).

Color-forming compounds which may be used according to the present invention are not particularly limited and may be ones generally used for pressure-sensitive recording paper or heat-sensitive recording paper. Specific examples of such color forming compounds include a fluoran-based compound, a triarylmethane-based compound, a spiro-based compound, a diphenylmethane-based compound, a thiazine-based compound, a lactam-based compound, and a fluorene-based compound.

Specific examples of the fluoran-based compound include 3-diethylamino-6-methyl-7-anilinofluoran, 3-dibutylamino-6-methyl-7-anilinofluoran, 3-(N-methyl-N-cyclohexylamino)-6-methyl-7-anilinofluoran, 3-(N-ethyl-N-isopentylamino)-6-methyl-7-anilinofluoran, 3-(N-ethyl-N-isobutylamino)-6-methyl-7-anilinofluoran, 3-[N-ethyl-N-(3-ethoxypropyl) amino]-6-methyl-7-anilinofluoran, 3-(N-ethyl-N-hexylamino)-6-methyl-7-anilinofluoran, 3-dipentylamino-6-methyl-7-anilinofluoran, 3-(N-methyl-N-propylamino)-6-methyl-7-anilinofluoran, 3-(N-ethyl-N-tetrahydrofurylamino)-6-methyl-7-anilinofluoran, 3-diethylamino-6-methyl-7-(p-chloroanilino) fluoran, 3-diethylamino-6-methyl-7-(p-fluoroanilino) fluoran, 3-[N- ethyl-N-(p-tolyl) amino]-6-methyl-7-anilinofluoran, 3-diethylamino-6-methyl-7-(p-toluidino) fluoran, 3-diethylamino-7-(o-chloroanilino) fluoran, 3-dibutylamino-7-(o-chloroanilino) fluoran, 3-diethylamino-7-(o-fluoroanilino)) fluoran, 3-dibutylamino-7-(o-fluoroanilino) fluoran, 3-diethylamino-7-(3,4-dichloroanilino) fluoran, 3-pyrrolidino-6-methyl-7-anilinofluoran, 3-diethylamino-6-chloro-7-ethoxyethylaminofluoran, 3-diethylamino-6-chloro-7-anilinofluoran, 3-diethylamino-7-chlorofluoran, 3-diethylamino-7-methylfluoran, 3-diethylamino-7-octylfluoran, and 3-[N-ethyl-N-(p-tolyl) amino]-6-methyl-7-phenethylfluoran, and 3-dibutylamino-6-methyl-7-anilinofluoran is preferable.

Specific examples of the triarylmethane-based compound include 3,3-bis(p-dimethylaminophenyl)-6-dimethylaminophthalide (synonym: crystal violet lactone or CVL), 3,3-bis(p-dimethylaminophenyl) phthalide, 3-(p-dimethylaminophenyl)-3-(1,2-dimethylaminoindol-3-yl) phthalide, 3-(p-dimethylaminophenyl)-3-(2-methylindol-3-yl) phthalide, 3-(p-dimethylaminophenyl)-3-(2-phenylindol-3-yl) phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-(2-phenylindol-3-yl)-5-dimethylaminophthalide, and 3-p-dimethylaminophenyl-3-(1-methylpyrrol-2-yl)-6-dimethylaminophthalide.

Specific examples of the spiro-based compound include 3-methylspirodinaphthopyran, 3-ethylspirodinaphthopyran, 3,3'-dichlorospirodinaphthopyran, 3-benzylspirodinaphthopyran, 3-propylspirobenzopyran, 3-methylnaphtho-(3-methoxybenzo) spiropyran, and 1,3,3-trimethyl-6-nitro-8'-methoxyspiro (indoline-2,2'-benzopyran). Specific examples of the diphenylmethane-based compound include N-halophenyl-leucoauramine, 4,4-bis-dimethylaminophenylbenzhydryl benzyl ether, and N-2,4,5-trichlorophenyl leucoauramine. Specific examples of the thiazine-based compound include benzoyl leucomethylene blue and p-nitrobenzoyl leucomethylene blue. Specific examples of the lactam-based compound include rhodamine B anilinolactam and rhodamine B-p-chloroanilinolactam. Specific examples of the fluorene-based compound include 3,6-bis(dimethylamino) fluorene spiro (9,3')-6'-dimethylaminophthalide, 3,6-bis(dimethylamino) fluorene spiro (9,3')-6'-pyrrolidinophthalide, and 3-dimethylamino-6-diethylaminofluorene spiro (9,3')-6'-pyrrolidinophthalide.

These color forming compounds are used singly or in combination thereof.

Other color developing agents which can be used in combination are not particularly limited and may be ones generally used for pressure-sensitive recording paper or heat-sensitive recording paper. Examples of such color developing agents include: a phenolic compound such as α-naphthol, β-naphthol, p-octylphenol, 4-t-octylphenol, p-t-butylphenol, p-phenylphenol, 1,1-bis(p-hydroxyphenyl) propane, 2,2-bis(p-hydroxyphenyl) propane (synonym: bisphenol A or BPA), 2,2-bis(p-hydroxyphenyl) butane, 1,1-bis(p-hydroxyphenyl) cyclohexane, 4,4'-thiobisphenol, 4,4'-cyclo-hexylidene diphenol, 2,2'-bis(2,5-dibromo-4-hydroxyphenyl) propane, 4,4'-isopropylidenebis(2-t-butylphenol), 2,2'-methylenebis(4-chlorophenol), 4,4'-dihydroxydiphenylsulfone, 4-hydroxy-4'-methoxydiphenylsulfone, 2,4'-dihydroxydiphenylsulfone, 4-hydroxy-4'-isopropoxydiphenylsulfone, 4-hydroxy-4'-ethoxydiphenylsulfone, 4-hydroxy-4'-butoxydiphenylsulfone, 4-hydroxy-4'-benzyloxydiphenylsulfone, methyl bis(4-hydroxyphenyl) acetate, butyl bis(4-hydroxyphenyl) acetate, benzyl bis(4-hydroxyphenyl) acetate and 2,4-dihydroxy-2'-methoxybenzanilide; an aromatic carboxylic acid derivative and an aromatic carboxylic acid, such as benzyl p-hydroxybenzoate, ethyl p-hydroxybenzoate, dibenzyl 4-hydroxyphthalate, dimethyl 4-hydroxyphthalate, ethyl 5-hydroxyisophthalate, 3,5-di-t-butylsalicylic acid and 3,5-di-α-methylbenzylsalicylic acid, and a polyvalent metal salt thereof; benzotriazole, and a benzotriazole derivative such as 5-methyl-1H-benzotriazole, 4-methyl-1H-benzotriazole, phenyl-6 benzotriazole, phenyl-5 benzotriazole, chloro-5 benzotriazole, chloro-5 methyl benzotriazole, chloro-5 isopropyl-7 methyl-4 benzotriazole and bromo-5 benzotriazole; saccharin, and a saccharin derivative such as 1-bromosaccharin, 1-nitrosaccharin and 1-aminosaccharin; a sulfonamide derivative such as methanylanilide, N-phenyl-4-aminobenzenesulfonamide, neourilon, N-phenyl-3-nitrobenzenesulfonamide, N-(4-methyl-2-nitrophenyl) benzenesulfonamide, N-(2-methoxyphenyl)-p-toluenesulfonamide, or N-(2-(3-phenylureido) phenyl) benzenesulfonamide; and a sulfonylurea derivative such as N-(p-toluenesulfonyl)-N'-(3-n-butylaminosulfonylphenyl) urea, N-(p-toluenesulfonyl)-N'-(4-trimethylacetophenyl) urea, N-(benzenesulfonyl)-N'-(3-p-toluenesulfonyloxyphenyl) urea, N-(p-toluenesulfonyl)-N'-(3-p-toluenesulfonylphenyl) urea, N-(p-toluenesulfonyl)-N'-(3-phenylsulfonyloxyphenyl) urea, tolbutamide, or chloropropamide.

Specific examples of sensitizers (heat fusible compound) which can be used according to the present invention include wax such as animal and vegetable wax and synthetic wax, a higher fatty acid, a higher fatty acid amide, a higher fatty acid anilide, a naphthalene derivative, an aromatic ether, an aromatic carboxylic acid derivative, an aromatic sulfonic acid ester derivative, a carbonic acid or oxalic acid diester derivative, a biphenyl derivative, a terphenyl derivative, and a sulfone derivative. Among these compounds, compounds which are a solid at normal temperature and have a melting point of 60° C. or higher are preferably used.

Specific examples of the wax include Japanese wax, carnauba wax, shellac, paraffin, a montan wax, oxidized paraffin, a polyethylene wax, and oxidized polyethylene. Examples of the higher fatty acid include stearic acid and behenic acid. Examples of the higher fatty acid amide include stearic acid amide, oleic acid amide, N-methyl stearic acid amide, erucic acid amide, methylol behenic acid amide, methylene bis stearic acid amide, and ethylene bis stearic acid amide. Examples of the higher fatty acid anilide include stearic acid anilide and linoleic acid anilide. Examples of the naphthalene derivative include 1-benzyloxynaphthalene, 2-benzyloxynaphthalene, and phenyl 1-hydroxy naphthoate. Examples of the aromatic ether include 1,2-diphenoxyethane, 1,4-diphenoxybutane, 1,2-bis (3-methylphenoxy) ethane, 1,2-bis(4-methoxyphenoxy) ethane, 1,2-bis(3,4-dimethylphenyl) ethane, 1-phenoxy-2-(4-chlorophenoxy) ethane, 1-phenoxy-2-(4-methoxyphenoxy) ethane, and 1,2-diphenoxymethylbenzene. Examples of the aromatic carboxylic acid derivative include benzyl p-hydroxybenzoate, benzyl p-benzyloxybenzoate, and dibenzyl terephthalate. Examples of the aromatic sulfonic acid ester derivative include phenyl p-toluenesulfonate, phenyl mesitylenesulfonate, and 4-methylphenyl mesitylenesulfonate. Examples of the carbonic acid or oxalic acid diester derivative include diphenyl carbonate, dibenzyl oxalate, di(4-chlorobenzyl) oxalate, and di(4-methylbenzyl) oxalate. Examples of the biphenyl derivative include p-benzylbiphenyl and p-allyloxybiphenyl. Examples of the terphenyl derivative include m-terphenyl. Examples of the sulfone derivative include diphenyl sulfone.

Specific examples of preservability improvers which can be used according to the present invention include: a hindered phenol compound such as 2,2'-methylenebis(4-methyl-6-t-butylphenol), 2,2'-methylenebis(4-ethyl-6-t-butylphenol), 2,2'-ethylidenebis(4,6-di-t-butylphenol), 4,4'-thiobis(2-methyl-6-t-butylphenol), 4,4'-butylidenebis(6-t-butyl-m-cresol), 1-[α-methyl-α-(4'-hydroxyphenyl) ethyl]-4-[α',α'-bis(4'-hydroxyphenyl) ethyl] benzene, 1,1,3-tris(2-methyl-4-hydroxy-5-cyclohexylphenyl) butane, 1,1,3-tris(2-methyl-4-hydroxy-5-t-butylphenyl) butane, tris(2,6-dimethyl-4-t-butyl-3-hydroxybenzyl) isocyanurate, 4,4'-thiobis(3-methylphenol), 4,4'-dihydroxy-3,3',5,5'-tetrabromodiphenylsulfone, 4,4'-dihydroxy-3,3',5,5'-tetramethyldiphenylsulfone, 2,2-bis(4-hydroxy-3,5-dibromophenyl) propane, 2,2-bis(4-hydroxy-3,5-dichlorophenyl) propane, or 2,2-bis(4-hydroxy-3,5-dimethylphenyl) propane; an epoxy compound such as 1,4-diglycidyloxybenzene, 4,4'-diglycidyloxydiphenylsulfone, 4-benzyloxy-4'-(2-methylglycidyloxy) diphenylsulfone, diglycidyl terephthalate, a cresol novolak type epoxy resin, a phenol novolak type epoxy resin, or a bisphenol A type epoxy resin; N,N'-di-2-naphthyl-p-phenylenediamine; sodium or a polyvalent metal salt of 2,2'-methylenebis(4,6-di-t-butylphenyl) phosphate; and bis(4-ethyleneiminocarbonyl aminophenyl) methane; a urea urethane compound (a color-developing agent UU manufactured by Chemipro Kasei Co., Ltd., and the like); a diphenyl sulfone crosslinking type compound represented by the following formula (1); and a mixture thereof.

[Chemical Formula 1]

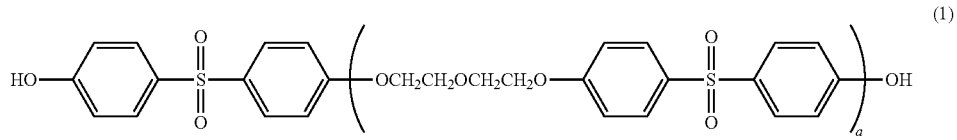

(1)

wherein a represents an integer of 0 to 6.

Specific examples of binders which can be used according to the present invention include: a water-soluble compound such as methyl cellulose, methoxy cellulose, hydroxyethyl cellulose, carboxymethyl cellulose, sodium carboxymethyl cellulose, cellulose, polyvinyl alcohol (PVA), carboxyl group-modified polyvinyl alcohol, sulfonic acid group-modified polyvinyl alcohol, silyl group-modified polyvinyl alcohol, polyvinyl pyrrolidone, polyacrylamide, polyacrylic acid, starch and a derivative thereof, casein, gelatin, a water-soluble isoprene rubber, an alkali salt of a styrene/maleic anhydride copolymer, or an alkali salt of an iso (or diiso) butylene/maleic anhydride copolymer; and a hydrophobic polymer emulsion such as a (meth)acrylate copolymer, a styrene/(meth)acrylate copolymer, polyurethane, a polyester-based polyurethane, polyether-based polyurethane, polyvinyl acetate, an ethylene/vinyl acetate copolymer, polyvinyl chloride, a vinyl chloride/vinyl acetate copolymer, polyvinylidene chloride, polystyrene, a styrene/butadiene (SB) copolymer, a carboxylated styrene/butadiene (SB) copolymer, a styrene/butadiene/acrylic acid-based copolymer, an acrylonitrile/butadiene (NB) copolymer, a carboxylated acrylonitrile/butadiene (NB) copolymer, or composite particles of colloidal silica and a (meth)acrylic resin.

Specific examples of the filler used in the present invention include calcium carbonate, magnesium carbonate, magnesium oxide, silica, white carbon, talc, clay, alumina, magnesium hydroxide, aluminum hydroxide, aluminum oxide, barium sulfate, a polystyrene resin, and a urea-formalin resin.

In the present invention, various additives other than those described above can be also used. Example of the additives include: a metal salt of a higher fatty acid, such as zinc stearate and calcium stearate, which can be used for preventing thermal head abrasion, sticking, or the like; an ultraviolet absorber, such as a phenol derivative, a benzophenone-based compound and a benzotriazole-based compound, which can be used for imparting an antioxidant or antiaging effect; various surfactants, and defoaming agents.

Next, methods for preparing heat-sensitive recording materials of the present invention and heat-sensitive recording sheets containing the same, such as heat-sensitive recording paper, will be described. According to one embodiment of the present invention, a heat-sensitive recording material can be manufactured, for example, by pulverizing and dispersing 3,3'-diallyl-4,4'-dihydroxydiphenylsulfone, a color forming compound, and a sensitizer respectively together with a binder or if necessary another additive or the like in a dispersing machine such as a ball mill, an attritor, or a sand mill to prepare a dispersion (usually water is used as a medium when pulverization or dispersion is performed in a wet manner), then mixing the dispersions to prepare a coating liquid. A heat-sensitive recording sheet having a heat-sensitive recording layer according to the present invention can be then manufactured by applying the coating liquid onto a support such as paper (plain paper, high quality paper, coated paper, or the like can be used), a plastic sheet, or synthetic paper with a bar coater, a blade coater or the like in such an amount to usually have a dry weight of 1 to 20 g/m$^2$, and drying the coating liquid.

In addition, if necessary, an intermediate layer may be disposed between the heat-sensitive recording layer and the support, or an overcoat layer (protective layer) may be disposed on the heat-sensitive recording layer. A heat-sensitive recording sheet containing the heat-sensitive recording material comprising the intermediate layer and the overcoat layer (protective layer) according to the present invention, is manufactured, for example, by performing pulverizing and dispersing the color-developing agent and a color forming compound together with the above-described binder or other additives if necessary, in the same way as the preparation of a coating liquid for the heat-sensitive recording layer, to prepare a coating liquid for an intermediate layer or a coating liquid for an overcoat layer (protective layer), then applying the coating liquid in such an amount to usually have a dry weight of 0.1 to 10 g/m$^2$, and then drying the coating liquid.

EXAMPLES

Hereinafter, the present invention will be described with reference to Examples, but it is to be noted that the present invention is not limited thereto. In Examples, "part(s)" means part(s) by mass and "%" means % by mass. The melting point of the following compound means an extrapolated onset melting temperature (Te) measured by a differential scanning calorimeter (hereinafter, abbreviated as DSC). 5 mg of a sample was measured and put into an aluminum crimp cell (P/N 201-52943), and DSC analysis was performed under a temperature rising condition of 10° C./min up to 100° C. and a temperature-rising conditions of 5° C./min at 100° C. or higher.

Synthesis Example 1

According to a method described in JP-B-3992252, 3,3'-diallyl-4,4'-dihydroxydiphenylsulfone was manufactured. The melting point of the obtained 3,3'-diallyl-4,4'-dihydroxydiphenylsulfone was 151.7° C. As a result of HPLC analysis, the content of a di-rearrangement product (main body) was 96.2%, and the content of a compound having a molecular weight of 660 was 0.8% in mass spectrometry. Powder X-ray diffraction measurement by a Cu-Kα ray indicated relatively strong peaks at diffraction angles (2θ) [° ] of 7.2, 14.5, 16.3, 18.0, 20.0, 21.0, 22.0, 24.7, and 29.0.

Example 1

The 3,3'-diallyl-4,4'-dihydroxydiphenylsulfone obtained in Synthesis Example 1 was purified by silica gel column chromatography. Methylene chloride was used as an eluent, and spherical silica gel for chromatography in the name of Wakosil C-200 (column manufactured by Wako Pure Chemical Industries) was used as silica gel in a column.

The melting point of the obtained 3,3'-diallyl-4,4'-dihydroxydiphenylsulfone was 152.6° C. As a result of HPLC analysis, the content of a di-rearrangement product (main body) was 96.8%, and the content of a compound having a molecular weight of 660 (abbreviated as MW 660 in Table 1 below) was 0.4%. Powder X-ray diffraction measurement by a Cu-Kα ray indicated relatively strong peaks at diffraction angles (2θ) [° ] of 7.2, 14.5, 16.3, 18.0, 20.0, 21.0, 22.0, 24.7, and 29.0.

Example 2

[Manufacture of Heat-Sensitive Recording Material]

The above 3,3'-diallyl-4,4'-dihydroxydiphenylsulfone obtained in Example 1 was pulverized and dispersed using a sand grinder so as to have an average particle size of 1 μm or less to prepare liquid [A].

Liquid [A]: 3,3'-diallyl-4,4'-dihydroxydiphenylsulfone obtained in Example 1 15 parts

| | |
|---|---|
| 25% PVA aqueous solution | 20 parts |
| water | 65 parts |

A mixture having the following composition was pulverized and dispersed using a sand grinder so as to have an average particle size of 1 μm or less to prepare liquid [B].

| | |
|---|---|
| Liquid [B]: 3-dibutylamino-6-methyl-7-anilinofluoran | 35 parts |
| 15% PVA aqueous solution | 40 parts |
| water | 25 parts |

Subsequently, each liquid obtained above and the following chemicals were mixed at the following ratio to prepare a coating liquid for a heat-sensitive recording layer. The coating liquid was applied onto high quality paper having a weight of 50 g/m² so as to have a dry weight of 5 g/m² and dried to form a heat-sensitive recording layer, thereby manufacturing heat-sensitive recording paper.

| | |
|---|---|
| Liquid [A] | 40.0 parts |
| Liquid [B] | 8.6 parts |
| 67% calcium carbonate aqueous dispersion | 9.0 parts |
| 48% modified styrene-butadiene copolymer latex | 6.3 parts |
| water | 36.1 parts |

(Formation of Protective Layer)

Next, a coating liquid for protective layer having the following ratio was applied onto the above heat-sensitive recording layer so as to have a dry weight of 2 g/m² and dried to form a protective layer.

| | |
|---|---|
| 40% styrene/acrylate copolymer emulsion | 115 parts |
| 5% bentonite aqueous dispersion | 17 parts |
| 45% styrene-acrylic copolymer aqueous emulsion | 44 parts |
| 39% zinc stearate aqueous dispersion | 103 parts |
| 67% calcium carbonate aqueous dispersion | 15 parts |

Comparative Example 1

Comparative heat-sensitive recording paper was manufactured in the same manner as that in Example 2 except that 3,3'-diallyl-4,4'-dihydroxydiphenylsulfone obtained in Synthesis Example 1 was used in place of 3,3'-diallyl-4,4'-dihydroxydiphenylsulfone obtained in Example 1.

[Plasticizer Resistance Test]

The above heat-sensitive recording papers obtained in Example 2 and Comparative Example 1 were provided for a thermal printer (TH-M2/PP) manufactured by Okura Engineering Co., Ltd. to prepare samples for evaluation which have a printed portion of a color formed with a pulse width of 1.2 msec. A vinyl chloride wrapping film (a wrapping film containing a plasticizer) was wrapped in triplicate on a glass plate, and the samples for evaluation were attached thereon respectively, and a vinyl chloride wrapping film was further wrapped in triplicate thereon. In this state, the resulting product was left at 45° C. for 24 hours. Macbeth reflection densities of the printed portions of the samples before and after the test were measured using a colorimeter in the trade name of "SpectroEye" manufactured by GRETAG-MACBETH. Colorimetry was performed using Illuminant C as a light source and ANSI A as a concentration standard under conditions of a viewing angle of 2 degrees. Results are indicated in Table 1 below. It is noted that the higher a residual ratio of a printed portion is, the better plasticizer resistance is. The residual ratio was determined by the following calculation formula.

Residual ratio (%)=(Macbeth reflection density of printed portion of sample after test)/(Macbeth reflection density of printed portion of sample before test)×100

[Hand Cream Resistance Test]

The above heat-sensitive recording papers obtained in Example 2 and Comparative Example 1 were provided for a thermal printer (TH-M2/PP) manufactured by Okura Engineering Co., Ltd. to prepare samples which have a printed portion of a color formed with a pulse width of 1.2 msec. The samples for evaluation were attached on a glass plate respectively. Two types of hand cream (1. MVNE body butter JA jasmine with apple manufactured by SPR Japan Co., Ltd., and 2. ATRIX hand cream B manufactured by Nivea Kao Corporation) were each applied onto the surfaces of the printed portions, and left at 45° C. for 24 hours. Macbeth reflection densities of the printed portions of the samples before and after the test were measured with a colorimeter in the trade name of "SpectroEye" manufactured by GRETAG-MACBETH. Colorimetry was performed using Illuminant C as a light source and ANSI A as a concentration standard under conditions of a viewing angle of 2 degrees. Results are indicated in Table 1 below. It is noted that the higher a residual ratio of a printed portion is, the better hand cream resistance is. The residual ratio was determined by the following calculation formula.

Residual ratio (%)=(Macbeth reflection density of printed portion of sample after test)/(Macbeth reflection density of printed portion of sample before test)×100

[Moist Heat Resistance Test]

The above heat-sensitive recording papers obtained in Example 2 and Comparative Example 1 were left for 1 hour in a moist heat resistance test machine (test condition: 60° C., 90% RH). A Macbeth reflection density of a background after the test was measured with a colorimeter in the trade name of "SpectroEye" manufactured by GRETAG-MACBETH. Colorimetry was performed using Illuminant C as a light source and ANSI A as a concentration standard under conditions of a viewing angle of 2 degrees. Results are indicated in Table 1 below. It is noted that the smaller a Macbeth reflection densitometer after the test is, the better moist heat resistance of a background is.

TABLE 1

| | Primary product Purity (%) | Compound having MW of 660 Content (%) | DSC melting point (° C.) | Plasticizer resistance | 1 Hand cream resistance Residual ratio (%) | 2 Hand cream resistance | Moist heat resistance Calorimetric value of background |
|---|---|---|---|---|---|---|---|
| Example 2 | 96.8 | 0.4 | 152.6 | 41 | 89 | 80 | 0.13 |
| Comparative Example 1 | 96.2 | 0.8 | 151.8 | 31 | 71 | 75 | 0.21 |

As is clear from the above evaluation results in Table 1, when a heat-sensitive recording material was manufactured with 3,3'-diallyl-4,4'-dihydroxydiphenylsulfone in which the content of a compound having a molecular weight of 660 was 0.4% by mass as a color developing agent according to the present invention could be provided a heat-sensitive recording material exhibiting better effects than a conventional product in terms of plasticizer resistance and hand cream resistance of a printed portion, and moist heat resistance of a background, having high sensitivity and less background fogging during wet heating, having excellent image preservation stability, and having higher practicality.

The invention claimed is:

1. A heat-sensitive recording sheet comprising a support and a heat-sensitive recording material on said support, wherein said heat-sensitive recording material comprises a color-forming compound and 3,3'-diallyl-4,4'-dihydroxydiphenylsulfone, wherein the content of a compound generated as a by-product during synthesis of the 3,3'-diallyl-4,4'-dihydroxydiphenylsulfone and having a molecular weight of 660 is 0.4% or less by mass in mass spectrometry, and wherein the 3,3'-diallyl-4,4'-dihydroxydiphenylsulfone has a crystal form characterized by an X-ray diffraction diagram having peaks at least at diffraction angles (2θ) [°] of 7.2 and 22.0 in a powder X-ray diffraction method with a Cu-Kα.

2. The heat-sensitive recording sheet according to claim 1, wherein the 3,3'-diallyl-4,4'-dihydroxydiphenylsulfone has a crystal form characterized by an X-ray diffraction diagram having peaks at least at diffraction angles (2θ) [°] of 7.2, 16.3, 20.0, 22.0, 24.7 and 29.0 in a powder X-ray diffraction method with a Cu-Kα ray.

3. The heat-sensitive recording sheet according to claim 1, wherein the 3,3'-diallyl-4,4'-dihydroxydiphenylsulfone has a crystal form characterized by an X-ray diffraction diagram having peaks at least at diffraction angles (2θ) [°] of 7.2, 14.5, 16.3, 18.0, 20.0, 21.0, 22.0, 24.7 and 29.0 in a powder X-ray diffraction method with a Cu-Kα ray.

4. A heat-sensitive recording paper comprising a paper support and a heat-sensitive recording layer comprising a heat-sensitive recording material on said paper support, wherein said heat-sensitive recording material comprises a color-forming compound and 3,3'-diallyl-4,4'-dihydroxydiphenylsulfone, wherein the content of a compound generated as a by-product during synthesis of the 3,3'-diallyl-4,4'-dihydroxydiphenylsulfone and having a molecular weight of 660 is 0.4% or less by mass in mass spectrometry, and wherein the 3,3'-diallyl-4,4'-dihydroxydiphenylsulfone has a crystal form characterized by an X-ray diffraction diagram having peaks at least at diffraction angles (2θ) [°] of 7.2 and 22.0 in a powder X-ray diffraction method with a Cu-Kα ray.

5. The heat sensitive recording paper of claim 4, wherein the 3,3'-diallyl-4,4'-dihydroxydiphenylsulfone has a crystal form characterized by an X-ray diffraction diagram having peaks at least at diffraction angles (2θ) [°] of 7.2, 16.3, 20.0, 22.0, 24.7, and 29.0 in a powder X-ray diffraction method with a Cu-Kα ray.

6. The heat sensitive recording paper of claim 4, wherein the 3,3'-diallyl-4,4'-dihydroxydiphenylsulfone has a crystal form characterized by an X-ray diffraction diagram having peaks at least at diffraction angles (2θ) [°] of 7.2, 14.5, 16.3, 18.0, 20.0, 21.0, 22.0, 24.7, and 29.0 in a powder X-ray diffraction method with a Cu-Kα ray.

7. A heat-sensitive recording film comprising a film support and a heat-sensitive recording layer comprising a heat-sensitive recording material on said film support, wherein said heat-sensitive recording material comprises a color-forming compound and 3,3'-diallyl-4,4'-dihydroxydiphenylsulfone, wherein the content of a compound generated as a by-product during synthesis of the 3,3'-diallyl-4,4'-dihydroxydiphenylsulfone and having a molecular weight of 660 is 0.4% or less by mass in mass spectrometry, and wherein the 3,3'-diallyl-4,4'-dihydroxydiphenylsulfone has a crystal form characterized by an X-ray diffraction diagram having peaks at least at diffraction angles (2θ) [°] of 7.2 and 22.0 in a powder X-ray diffraction method with a Cu-Kα ray.

8. The heat sensitive recording film according to claim 7, wherein the 3,3'-diallyl-4,4'-dihydroxydiphenylsulfone has a crystal form characterized by an X-ray diffraction diagram having peaks at least at diffraction angles (2θ) [° ] of 7.2, 16.3, 20.0, 22.0, 24.7, and 29.0 in a powder X-ray diffraction method with a Cu-Kα ray.

9. The heat sensitive recording film according to claim 7, wherein the 3,3'-diallyl-4,4'-dihydroxydiphenylsulfone has a crystal form characterized by an X-ray diffraction diagram having peaks at least at diffraction angles (2θ) [° ] of 7.2, 14.5, 16.3, 18.0, 20.0, 21.0, 22.0, 24.7, and 29.0 in a powder X-ray diffraction method with a Cu-Kα ray.

10. A heat-sensitive recording sheet comprising a plastic sheet and a heat-sensitive recording layer comprising a heat-sensitive recording material on said plastic sheet, wherein said heat-sensitive recording material comprises a color-forming compound and 3,3'-diallyl-4,4'-dihydroxydiphenylsulfone, wherein the content of a compound generated as a by-product during synthesis of the 3,3'-diallyl-4,4'-dihydroxydiphenylsulfone and having a molecular weight of 660 is 0.4% or less by mass in mass spectrometry, and wherein the 3,3'-diallyl-4,4'-dihydroxydiphenylsulfone has a crystal form characterized by an X-ray diffraction diagram having peaks at least at diffraction angles (2θ) [°] of 7.2 and 22.0 in a powder X-ray diffraction method with a Cu-Kα ray.

11. The heat-sensitive recording sheet of claim 10, wherein the 3,3'-diallyl-4,4'-dihydroxydiphenylsulfone has a crystal form characterized by an X-ray diffraction diagram having peaks at least at diffraction angles (2θ) [° ] of 7.2, 14.5, 16.3, 18.0, 20.0, 21.0, 22.0, 24.7, and 29.0 in a powder X-ray diffraction method with a Cu-Kα ray.

12. The heat-sensitive recording sheet of claim 10, wherein the 3,3'-diallyl-4,4'-dihydroxydiphenylsulfone has a crystal form characterized by an X-ray diffraction diagram having peaks at least at diffraction angles (2θ) [° ] of 7.2, 16.3, 20.0, 22.0, 24.7, and 29.0 in a powder X-ray diffraction method with a Cu-Kα ray.

* * * * *